United States Patent
Ahola et al.

(10) Patent No.: US 7,917,198 B2
(45) Date of Patent: Mar. 29, 2011

(54) CALIBRATION OF PERFORMANCE MONITOR

(75) Inventors: Onni Ahola, Oulu (FI); Mika Niemimäki, Haukipudas (FI); Jarmo Mäentausta, Espoo (FI); Arto Niva, Jääli (FI); Hannu Kinnunen, Oulu (FI); Jari Miettinen, Oulu (FI)

(73) Assignee: Polar Electro Oy, Kempele (FI)

( * ) Notice: Subject to any disclaimer, the term of this patent is extended or adjusted under 35 U.S.C. 154(b) by 185 days.

(21) Appl. No.: 11/803,713

(22) Filed: May 15, 2007

(65) Prior Publication Data

US 2007/0276200 A1  Nov. 29, 2007

(30) Foreign Application Priority Data

May 18, 2006  (FI) .................................... 20065334

(51) Int. Cl.
*A61B 5/0402*  (2006.01)
(52) U.S. Cl. ...................................................... 600/519
(58) Field of Classification Search .................. 600/519
See application file for complete search history.

(56) References Cited

U.S. PATENT DOCUMENTS

| | | | |
|---|---|---|---|
| 4,566,461 A * | 1/1986 | Lubell et al. ................. | 600/481 |
| 5,318,596 A | 6/1994 | Barreras et al. | |
| 6,132,337 A | 10/2000 | Krupka et al. | |
| 6,513,532 B2 * | 2/2003 | Mault et al. ................. | 600/595 |
| 2001/0016689 A1 | 8/2001 | Heikkila et al. | |
| 2003/0065257 A1 | 4/2003 | Mault et al. | |
| 2004/0015195 A1 | 1/2004 | Daum et al. | |
| 2004/0077954 A1 | 4/2004 | Oakley et al. | |
| 2005/0033200 A1 | 2/2005 | Soehren et al. | |
| 2005/0054938 A1 | 3/2005 | Wehman et al. | |

OTHER PUBLICATIONS

American Heart Association/American Stroke Association; "What is a Stress Test?", pp. 1-2 (2007).

* cited by examiner

*Primary Examiner* — Eric D. Bertram
(74) *Attorney, Agent, or Firm* — Hoffmann & Baron, LLP

(57) ABSTRACT

In the solution of the invention, an association is formed between activity information characterizing the activity level of a user and a performance parameter value proportional to the heart rate information of the user, the activity information and heart rate information having been measured in a user-specific performance monitor, and the heart rate information being responsive to the activity level.

12 Claims, 4 Drawing Sheets

CALIBRATION OF PERFORMANCE MONITOR

CROSS-REFERENCE TO RELATED APPLICATION

This application claims priority to Finnish Patent Application Ser. No. 20065334, filed on May 18, 2006, which is incorporated herein by reference.

BACKGROUND OF THE INVENTION

1. Field of the Invention

The invention relates to a method of calibrating a user-specific performance monitor, a user-specific performance monitor, and a computer software product that contains encoded instructions for executing a computer process in a digital processor, the computer process calibrating the user-specific performance monitor.

2. Description of the Related Art

In activity measurement, the motion state of the user of a user-specific performance monitor is measured to determine the activity level of the user. The performance parameters characterizing the performance and obtained on the basis of the activity measurement do not, however, provide realistic results. Therefore, it is beneficial to examine means for calibrating the user-specific performance monitor.

SUMMARY OF THE INVENTION

It is an object of the invention to implement a method, user-specific performance monitor, and a computer software product so as to improve the accuracy of performance parameter values determined by activity measurement.

As a first aspect of the invention, a method is presented for calibrating a user-specific performance monitor, the method forming an association between activity information characterizing the activity level of the user and a performance parameter value proportional to the heart rate information of the user, the activity information and heart rate information having been measured by the user-specific performance monitor, and the heart rate information being responsive to the activity level.

As a second aspect of the invention, a user-specific performance monitor is presented, the monitor comprising: performance parameter determination means for determining a performance parameter value proportional to heart rate information of a user; activity measurement means for measuring activity information characterizing the activity level of the user; and association means for forming an association between the activity information and performance parameter value proportional to the heart rate information that is responsive to the activity level.

As another aspect of the invention, a computer software product is presented comprising encoded instructions for executing a computer process in a digital processor, the computer process calibrating a user-specific performance monitor and forming an association between activity information characterizing the activity level of the user and a performance parameter value proportional to the heart rate information of the user, the activity information and heart rate information having been measured by the user-specific performance monitor and the heart rate information being responsive to the activity level.

Preferred embodiments of the invention are described in the dependent claims.

The invention is based on associating activity information obtained from an activity measurement with a performance parameter value obtained from heart rate information, whereby the calibration of a user-specific performance monitor is achieved, in which by means of activity information and association information it is possible to determine a performance parameter value.

The method, user-specific performance monitor, and computer software product of the invention provide several advantages. One advantage is calibration, by means of which it is possible to determine a performance parameter value by using activity information and association information without measuring the heart rate.

BRIEF DESCRIPTION OF THE DRAWINGS

The invention will now be described in greater detail by means of preferred embodiments and with reference to the attached drawings, in which.

DETAILED DESCRIPTION OF THE PREFERRED EMBODIMENTS

Figure 1:
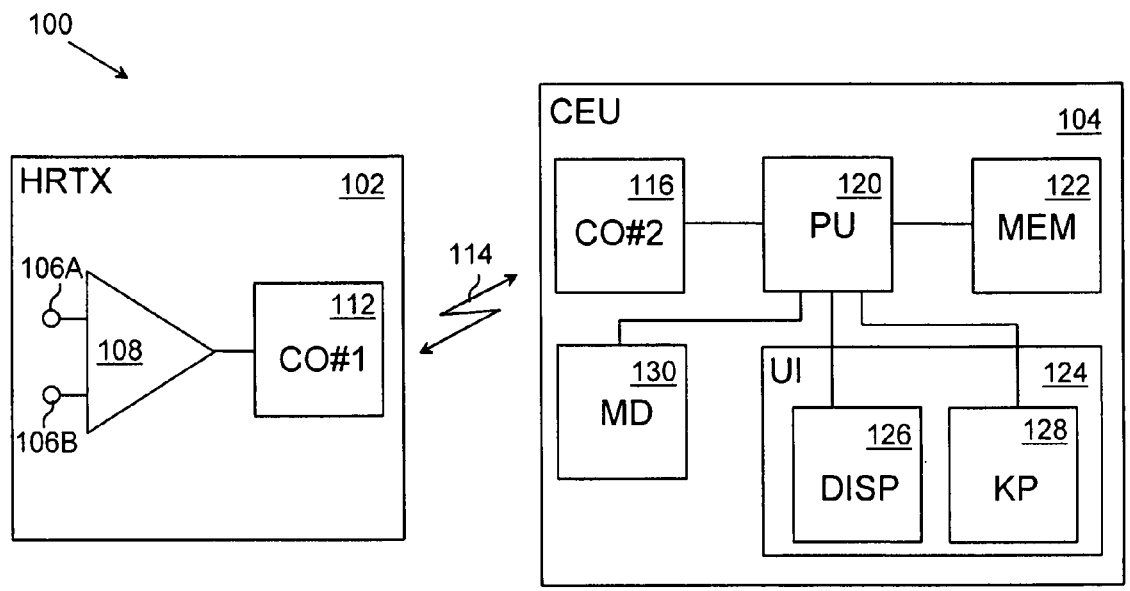
FIG. 1 shows a first example of the structure of a performance monitor.

FIG. 1 shows an example of the structure of a user-specific performance monitor 100. In this context, the user-specific performance monitor 100 is referred to as a performance monitor 100. The performance monitor 100 typically comprises electrodes 106A, 106B, an ECG preamplifier 108 (ECG, electrocardiogram), a first communication unit (CO#1) 112, a second communication unit (CO#2) 116, a processing unit (PU) 120, a memory unit (MEM) 122, a motion measuring unit (MMU) 130, and a user interface (UI) 124.

The electrodes 106A, 106B typically detect the electric potential difference generated by the electric activity of the heart muscle and generate an ECG signal characterizing the electric activity of the heart muscle. The ECG signal is input to the ECG preamplifier 108 from the electrodes 106A, 106B.

The ECG preamplifier 108 preamplifies the ECG signal and inputs the preamplified ECG signal to the first communication unit 112. The first communication unit 112 may comprise several successive amplifier stages, such as an AGC (Automatic Gain Control) amplifier and a power amplifier.

The first communication unit 112 generates a signal 114 transferring ECG information. The ECG information may, for example, use the ECG as such, part of the ECG, and/or timing information of the heart rate. The timing information may contain a timing pulse that represents the timing of a predetermined part of the ECG.

The signal 114 transferring ECG information is an electromagnetic wave propagating in the air or in a conductor, for instance.

The second communication unit 116 receives the signal 114 transferring ECG information and inputs the ECG information to the processing unit 120, which executes a computer process according to encoded □ctive□tions stored in the memory unit 122.

The processing unit 120 may be implemented by using analogue circuits, ASIC circuits (Application Specific Integrated Circuit), a digital processor, memory, and computer software. The processing unit 120 may form part of the computer of the performance monitor 100.

In one embodiment, the motion measuring unit 130 comprises a motion-sensitive sensor, such as acceleration sensor, that registers the movement of the user in one or more directions. The acceleration sensor transforms the acceleration caused by a movement or gravity into an electric signal.

In one embodiment, the acceleration sensor 130 is based on piezo-resistor technology that uses a material whose resistance changes as the material compresses. The acceleration of mass produces a force directed to the piezo resistor and, when directing a constant current through the piezo resistor, the voltage over the piezo resistor changes according to the compression caused by the acceleration.

In piezo-electric technology, a piezo-electric sensor generates a charge when the acceleration sensor is accelerated.

In silicon-bridge technology, a silicon chip is etched in such a manner that a silicon mass remains on the silicon chip at the end of a silicon beam. When acceleration is directed to the silicon chip, the silicon mass directs a force to the silicon beam, whereby the resistance of the silicon beam changes.

Micro-machined silicon technology is based on the use of a differential capacitor. Voice coil technology is based on the same principle as microphone. Examples of suitable motion detectors include Analog Devices ADXL105, Pewatron HW, or VTI Technologies SCA series.

The motion measuring unit 130 may also be based on other technologies suitable for the purpose, such as a gyroscope integrated on a silicon chip, a micro-vibration switch placed in a surface-mounting component, a mechanical pendulum, or a magnetic field-sensitive sensor.

The motion information generated by the motion measuring unit 130 may be transmitted to the processing unit 120 or memory unit 122.

The user interface 124 typically comprises a display unit (DISP) 126 and a display controller. The display unit 126 may contain LCD components (Liquid Crystal Display), for instance. The display unit 126 may display exercise instructions to the user graphically and/or numerically.

The user interface 124 may further comprise a keypad (KP) 128, by means of which the user may input commands to the performance monitor 100.

The performance monitor 100 shown in FIG. 1 may be divided into a heart rate transmitter (HRTX) 102 and a central processing unit (CEU) 104. The heart rate transmitter 102 typically comprises device parts 106A to 112 and performs ECG measurement and transmission of ECG information to the central processing unit 104. In some embodiments, the heart rate transmitter 102 may comprise a heart rate detector that detects a predetermined part of the ECG, generates a transmitter burst and/or bit stream representing the timing of a predetermined part of the ECG, and transmits the transmitter burst to the central processing unit 104 or, for example, to the second communication unit 116 positioned in the server.

The central processing unit 104 typically comprises device parts 116 to 130 that process the signal 114 transmitting ECG information and implement the user interface 124 and the motion measuring unit 130.

The central processing unit 104 is a wrist device, for example, that is positioned on the wrist of a user. The motion measuring unit 130 may then be configured to measure the movement of the user's upper limb.

Figure 2:
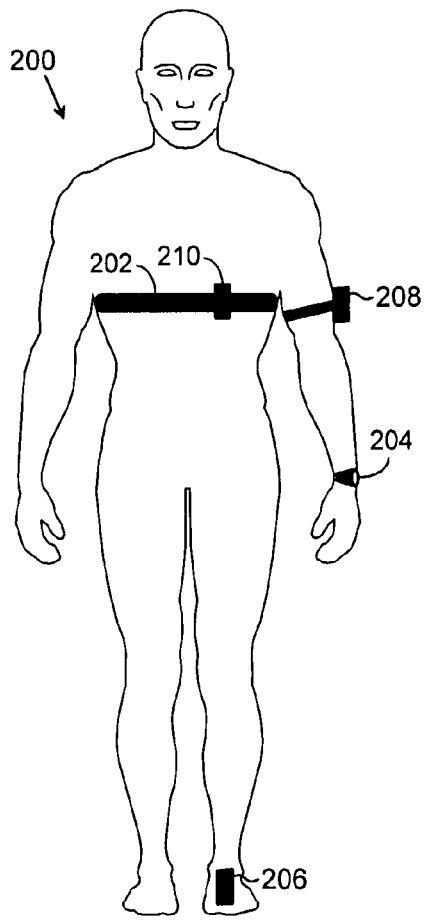
FIG. 2 shows a second example of the structure of a performance monitor.

Referring to the embodiment of FIG. 2, the heart rate transmitter 102 is positioned in a transmitter belt 202 around a user's 200 chest. The ECG information may be transmitted telemetrically, optically, or galvanically from the heart rate transmitter belt 202 to a central processing unit 204 that may be a wrist device positioned around the user's wrist. However, the presented solution is not restricted to a wrist device.

In one embodiment, the motion measuring unit 130 is positioned in a lower limb sensor 206 placed on the lower limb of the user 200.

In one embodiment, the motion measuring unit 130 is positioned in an upper limb sensor 208 placed on the upper limb of the user 200.

In one embodiment, the motion measuring unit 130 is positioned in a belt sensor 210 placed on the upper body of the user 200.

Figure 3:
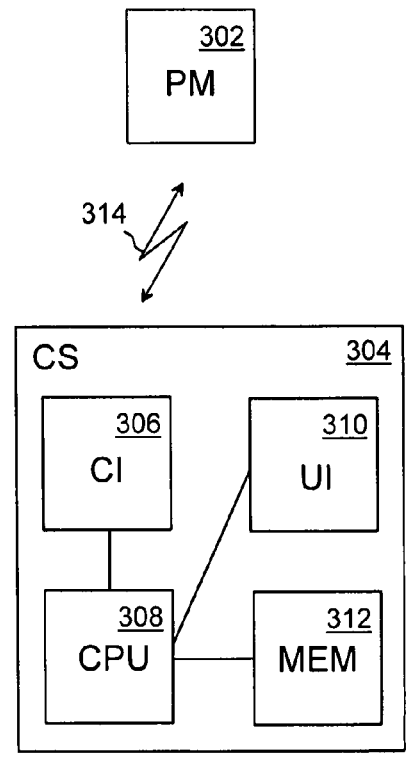
FIG. 3 shows an example of a system.

Referring to the example of FIG. 3, a system 300 may comprise a performance monitor (PM) 302 and a calculation system (CS) 304. The performance monitor 302 may exchange performance information, such as heart rate information, activity information measured by the performance monitor 302 and/or performance parameter values, with the calculation system 304 via a performance information signal 314.

Heart rate information comprises part of an ECG signal, timing information of the ECG, heart rate frequency, and/or heart rate interval, for example.

Activity information comprises acceleration components determined by the motion measuring unit 130, pulse timings, pulse magnitudes, number of pulses measured over an integration time, pulse power, pulse strength, pulse frequency, or any motion quantity characterizing activity, for example.

The performance parameter value is proportional to the heart rate information of the user. The performance parameter characterizes heart rate frequency, heart rate interval, energy consumption, condition, and/or stress level of the user, for example.

The calculation system 304 typically comprises a communication interface (CI) 306, a central processing unit (CPU) 308, a memory unit (MEM) 312, and a user interface (UI) 310.

The communication interface 306 implements the reception and transmission of a performance information signal 314. The communication interface 306 is, for instance, a wireless interface, such as radio interface, optical interface, or audio interface. In one embodiment, the communication interface 306 is a cable interface.

The central processing unit 308 executes a computer process according to the encoded instructions stored in the memory unit 312.

The calculation system 304 may be implemented by means of a computer and software, for example. The communication interface 306 may be integrated into the calculation system 304, or it may be a peripheral device to be connected to the calculation system 304.

The calculation system 304 may also be implemented by means of a portable communication device, such as mobile phone or PDA device (Personal Digital Assistant).

Figure 4:
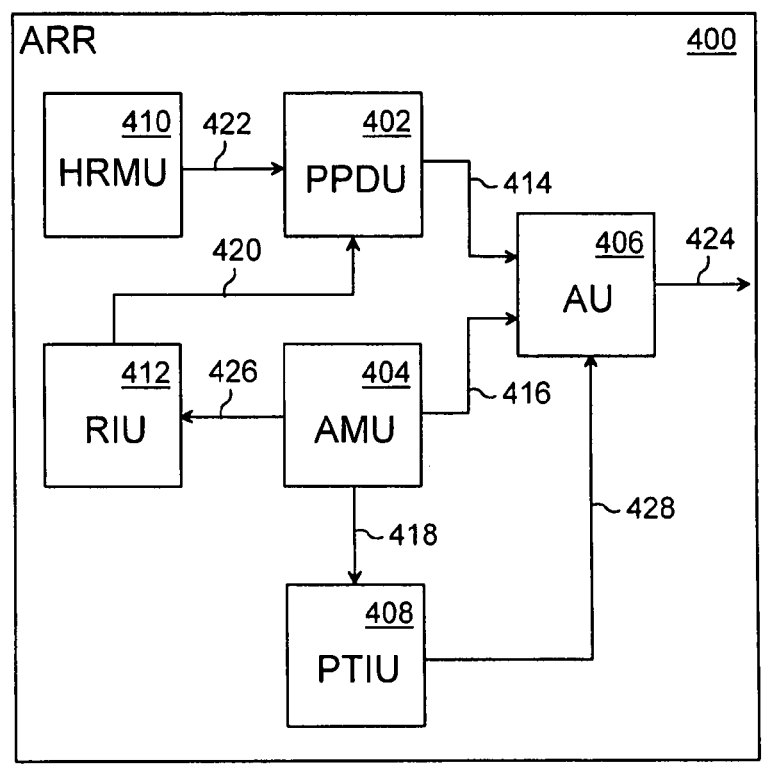
FIG. 4 shows an example of an arrangement.

With reference to FIG. 4, an arrangement (ARR) 400 is examined that comprises a performance parameter determination unit (PPDU) 402, an activity determination unit (AMU) 404, and an association unit (AU) 406.

The performance parameter determination unit 402 determines a performance parameter value 414 proportional to heart rate information 422 of the user, and inputs the performance parameter value 414 into the association unit 406.

The performance parameter determination unit 402 may receive heart rate information 422 from a heart rate measuring unit (HRMU) 410. The heart rate information 422 comprises the timing of the heart rate pulses, heart rate frequency, and/or heart rate interval, for instance.

In one embodiment, the performance parameter value 414 proportional to the heart rate information 422 is the heart rate frequency.

In one embodiment, the performance parameter value 414 proportional to the heart rate information 422 is the energy consumption of the user achieved with a specific heart rate frequency or heart rate frequency range. The performance parameter determination unit 402 then receives the heart rate frequency as the heart rate information 422 and determines the energy consumption corresponding to the heart rate frequency by means of the relation between the heart rate frequency and energy consumption stored in the performance parameter determination unit 402. The relation can be presented using a mathematical formula or table, and the relation may be influenced by factors characterizing the user, such as age, weight, height, sex, and possibly heart rate limits determined by the performance monitor 100, such as maximum heart rate, condition, or stress level.

The activity determination unit 404 measures activity information 416 characterizing the activity level of the user and inputs the activity information 416 to the association unit 406. In this context, the activity level of the user refers to physical activity that is expressed by physical movements generated by the user.

The activity information 416 comprises pulse information measured from the user's upper limb, for instance, and may be presented as a pulse frequency and/or pulse power.

Heart rate information 422 is responsive to the activity level, whereby a change in the activity level is reflected as a change in the user's heart rate information. Because the performance parameter value 414 is proportional to the heart rate information 422, there is a correlation between the activity information 416 and performance parameter value 414.

The association unit 406 generates association information 424 which associates the activity information 416 with the performance parameter value 414. The generation of the association information 424 makes it possible to calibrate the performance monitor 100 such that heart rate information can be presented by means of the activity information.

When the association information has been generated, the association unit 406 may, in one embodiment, determine the performance parameter value by using activity information 416 measured by the activity determination unit 404 and association information stored in the association unit 406. The performance parameter value may then, after the calibration, be determined without heart rate measurement, and the need for a transmitter belt 202 may be limited to performing the calibration only. The performance monitor 100 may thus be used only as a wrist device, for instance.

In one embodiment, the calibration range of the performance monitor 100 is limited to heart rate frequencies higher than a predefined limit. In one embodiment, the predefined limit is 100 p/min (pulses per minute). In a second embodiment, the predefined limit is 50% of the user's maximum heart rate.

The association between the activity information 416 and performance parameter value 414 may be implemented by parametrizing the relation between the activity information 416 and performance parameter information 414. Polynomial representation, for instance, may be used in parametrizing. The parameters may be used in connection with a return algorithm in such a manner that the algorithm returns a performance parameter value corresponding to a random activity information element when the random activity information element is input in the algorithm.

In one embodiment, the association between the activity information 416 and performance parameter value 414 is implemented with a table data structure, in which a performance parameter value 414 corresponding to an activity level is associated with each activity information element. In connection with a table data structure, it is possible to use an interpolation algorithm that helps determine a performance parameter value corresponding to a random activity information element, even though said activity information element and corresponding performance parameter value did not exits in the table data structure.

The performance parameter determination unit 402 may be implemented by means of a computer program executed in the processing unit 120 and stored in the memory unit 122 of the performance monitor 100 of FIG. 1.

The activity determination unit 404 can be implemented by means of the motion measuring unit 130 of the performance monitor 100 shown in FIG. 1. The functions of the activity determination unit 404 may also be executed by means of a computer program executed in the processing unit 120 and stored in the memory unit 122 of the performance monitor 100.

The association unit 406 may be implemented by means of a computer program executed in the processing unit 120 and stored in the memory unit 122 of the performance monitor 100 of FIG. 1.

In one embodiment, the association unit 406 is implemented by means of a computer program executed in the central processing unit 308 and stored in the memory unit 312 of the calculation system 304. The performance parameter value 414 and the activity information 416 are then determined in the performance monitor 100 and transferred to the calculation system 304 through a performance information signal 314. The association unit 406 implemented in the calculation system 304 generates the association information and may transfer it to the performance monitor 100 through a performance information signal 314.

Figure 5:
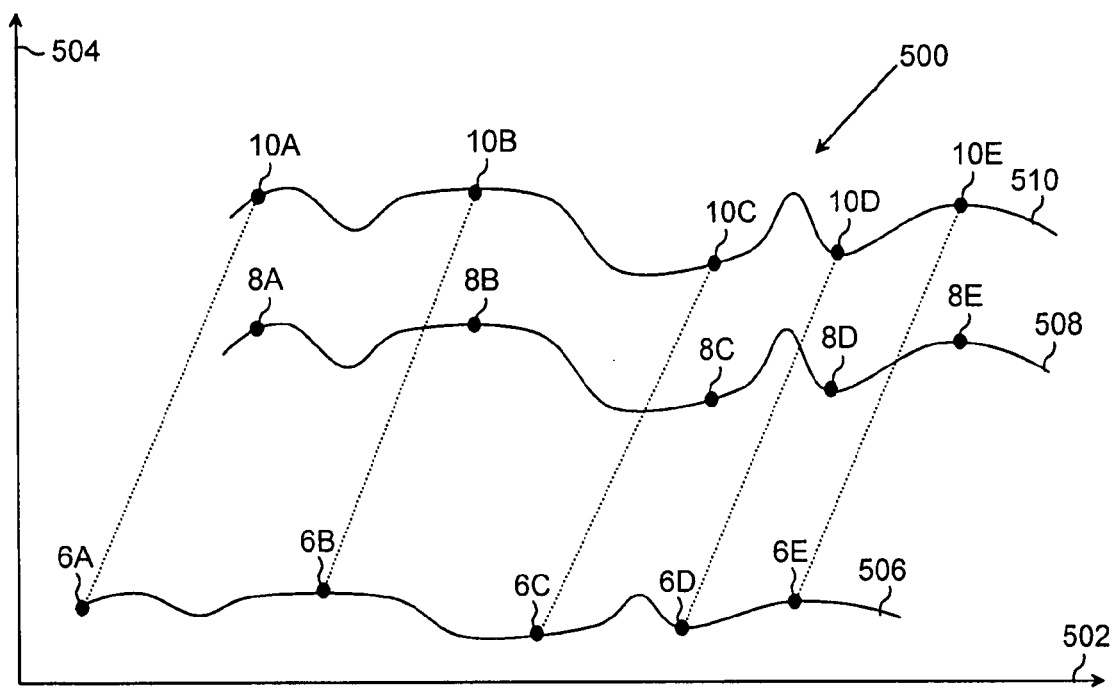
FIG. 5 shows a first example of a set of curves.

With reference to FIG. 5, a set of curves 500 is presented containing an activity information curve 506, heart rate information curve 508, and performance parameter curve 510.

The horizontal axis 502 depicts time in minutes, for instance. The vertical axis 504 is a generic axis depicting the heart rate information, activity information, and performance parameter value. The heart rate information may be shown in p/min, for instance, the activity information in p/min, for instance stance, and the performance parameter value may be shown in p/min or an energy unit.

The activity information curve 506 is determined by activity information elements 6A to 6E that are measuring points measured by the activity determination unit 404. Each activity information element 6A to 6E may represent a mean value of activity, which integrates the pulse power and/or pulse frequencies registered during two minutes, for instance.

The heart rate information curve 508 is determined by the heart rate information elements 8A to 8E that are measuring points measured by the heart rate measuring unit 410. Each heart rate information element 8A to 8E may represent integrated heart rate information, in which the integration time is 30 s, for instance.

The performance parameter curve 510 is determined by the performance parameter values 10A to 10E that are proportional to the heart rate information elements 8A to 8E. The performance parameter value 10A to 10E may be determined from the integrated heart rate information.

In one embodiment, the association unit 406 takes into account the delay between the activity information and heart rate information when forming the association. The performance parameter value 10A to 10E is typically temporally behind the corresponding activity information element 6A to 6E, and each activity information element 6A to 6E is then associated with a performance parameter values 10A to 10E defined later by an assumed or defined time interval. In the representation of FIG. 5, the activity information elements 6A to 6E to be associated with each other are connected by a dashed line with the corresponding performance parameter value 10A to 10E, when the delay has been taken into consideration. The delay is typically dozens of seconds or minutes depending on the activity level. In one embodiment, the delay is 3 minutes.

Figure 6:
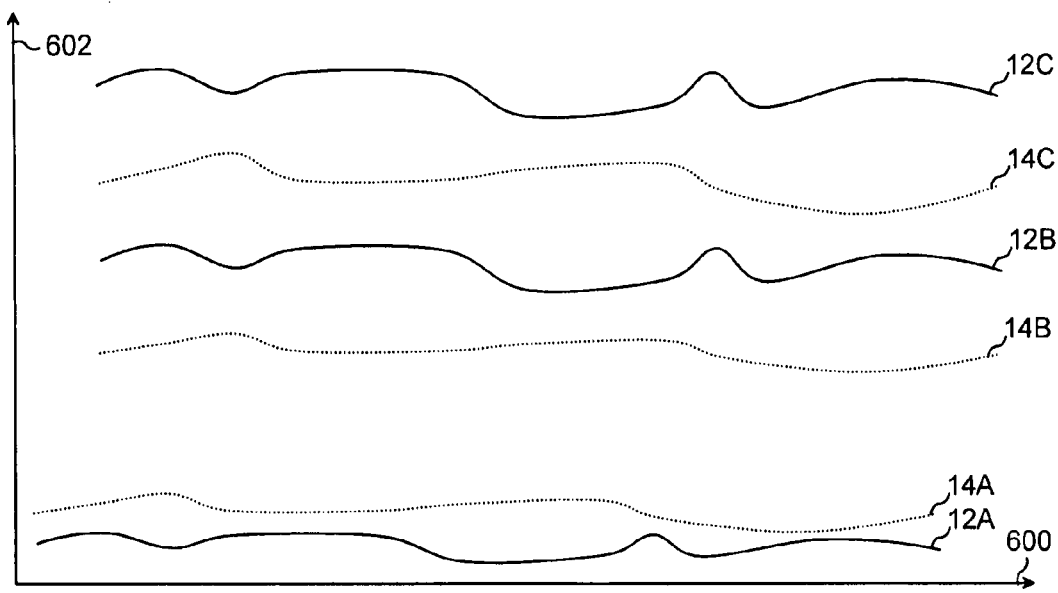
FIG. 6 shows a second example of a set of curves.

With reference to FIG. 6, let us examine a set of curves that comprises activity information curves 12A, 14A, heart rate information curves 12B, 14B, and performance parameter curves 12C, 14C. The horizontal axis 600 displays time using a random unit, and the vertical axis 602 is a generic axis displaying heart rate information, activity information, and a performance parameter value.

The curves 12A, 12B, 12C marked with a continuous line represent activity information, heart rate information, and energy consumption in a first performance type, such as badminton.

The curves 14A, 14B, 14C marked with a dotted line represent activity information, heart rate information, and energy consumption in a second performance type, such as walking.

On the basis of curves 12A, 14A, the activity level is similar in the first and second performance types. The heart rate level and energy consumption corresponding to the activity level in the first performance type are higher than in the second performance type because of the properties characteristic of the performance type.

With reference to the example of FIG. 4, in one embodiment the arrangement 400 comprises a performance type identification unit (PTIU) 408 that identifies the performance on the basis of the activity information 418 of the performance type.

The performance type may be running, walking, a ball game, or bicycling, for instance. The performance type may also specify a performance platform, in which case running on hard ground belongs to a different performance type than running on soft ground.

Identifying the performance type may be based on the rhythmics of the performance determined by the activity information 418 and/or the amplitude of the user's limbs.

When the performance type is identified, the performance type-specific activity information 416 and the performance type-specific performance parameter value 414 may be transmitted to the association unit 406 that forms a performance type-specific association between the performance type-specific activity information 416 and the performance type-specific performance parameter value 414. At the same time, the performance type identification unit 408 may also input into the association unit identification information 428 for the performance type. A table data structure or parametrization can then be generated for the performance type, in other words, a performance type-specific calibration. For instance, this corresponds to associating the activity information 14A of FIG. 6 to heart rate information 14B and energy consumption 14C.

When utilizing performance type-specific calibration, the performance type identification unit 408 identifies the type of the performance and inputs its identifier 428 to the association unit 406. The association unit 406 uses an association according to the performance type identifier 428 when determining the performance parameter value from the activity information 416.

The performance type identification unit 408 may be implemented by means of a computer program executed in the processing unit 120 and stored in the memory unit 122 of the performance monitor 100.

In one embodiment, the performance type identification unit 408 is implemented by means of a computer program executed in the central processing unit 308 and stored in the memory unit 312 of the calculation system 304.

In one embodiment, the arrangement 400 comprises a rest state identification unit (RIU) 412 that identifies the rest state of the user on the basis of the activity information 426. In identifying the rest state, the activity information 426 may be compared with a threshold value characterizing rest state. A rest state criterion may be met, for instance, when the activity level is lower than the threshold value during a predefined time interval. The rest state identification unit 412 may then transmit a signal 420 indicating rest state to the performance parameter determination unit 402 that determines the performance parameter value, such as energy consumption, in the user's rest state.

The rest state identification unit 412 may be implemented by means of a computer program executed in the processing unit 120 and stored in the memory unit 122 of the performance monitor 100.

In one embodiment, the rest state identification unit 412 is implemented by means of a computer program executed in the central processing unit 308 and stored in the memory unit 312 of the calculation system 304.

Figure 7:
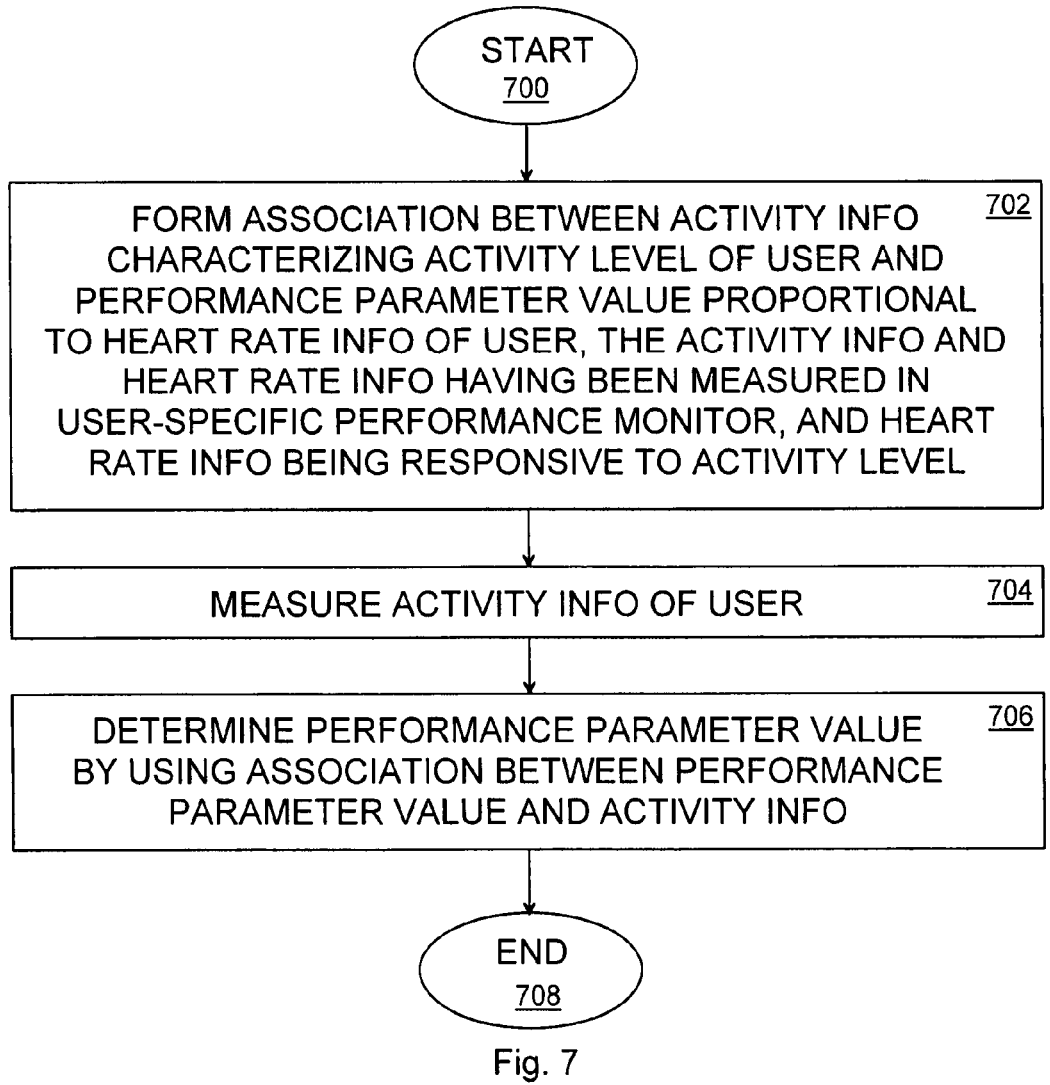
FIG. 7 shows an example of a method and/or computer process according to a first embodiment of the invention.
Figure 8:
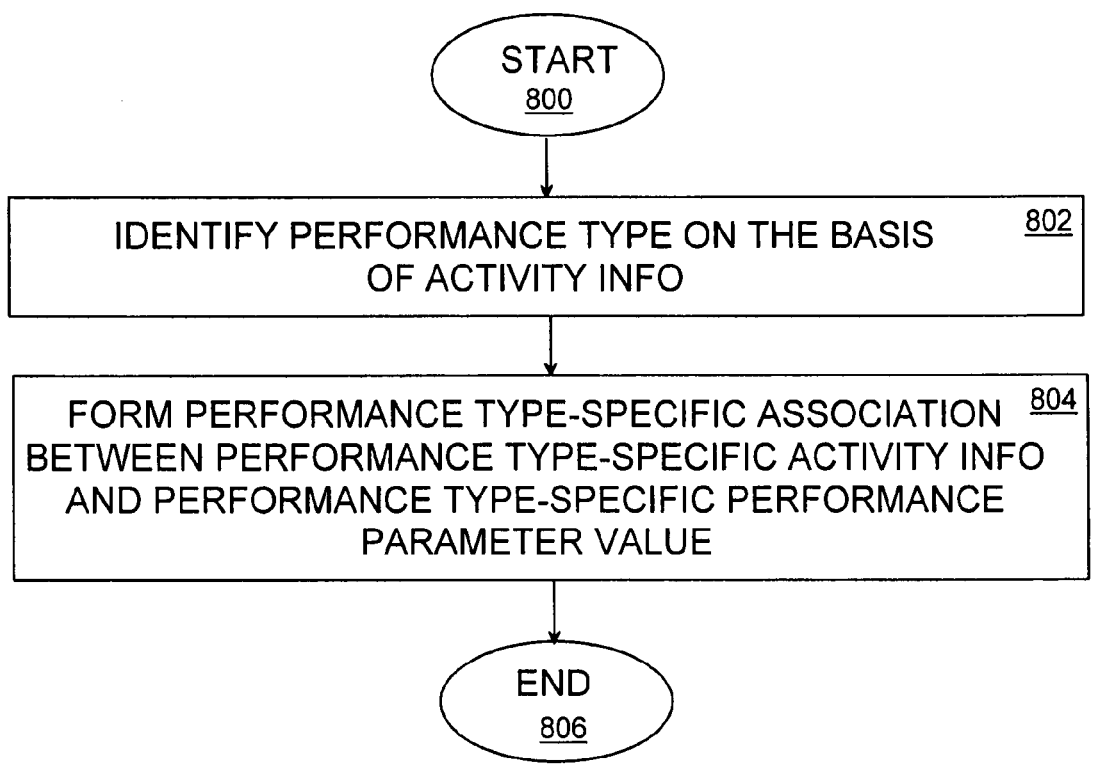
FIG. 8 shows an example of a method and/or computer process according to a second embodiment of the invention.
Figure 9:
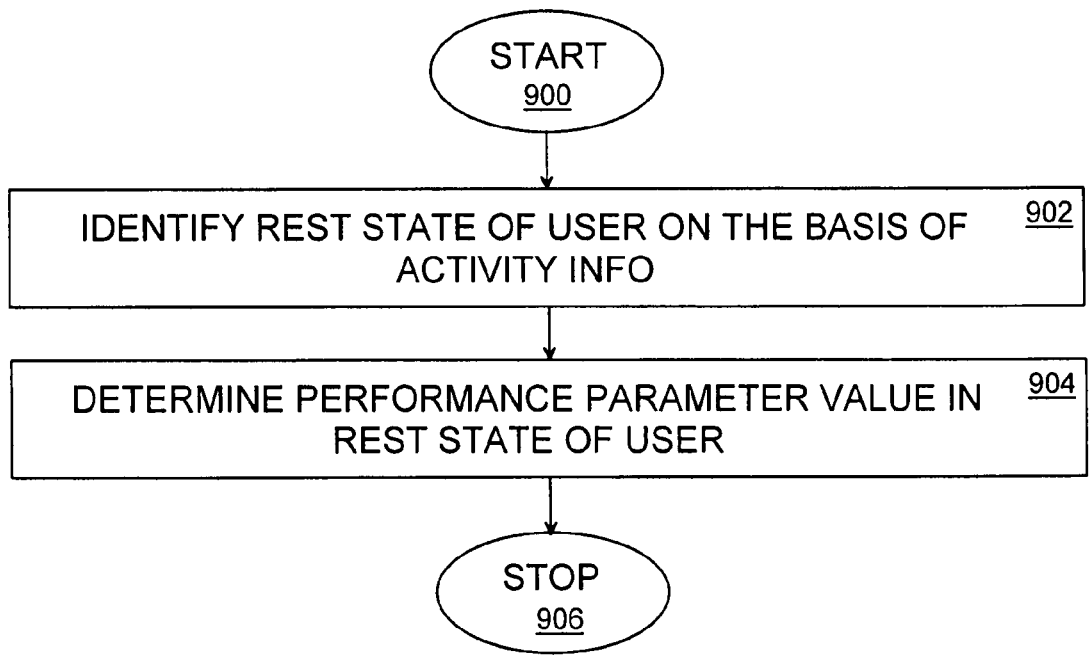
FIG. 9 shows an example of a method and/or computer process according to another embodiment of the invention.

Methods of some embodiments of the invention are examined with reference to FIGS. 7, 8, and 9.

With reference to FIG. 7, the method starts in 700.

In 702, an association is formed between activity information characterizing the activity level of the user and a performance parameter value proportional to the heart rate information of the user, the activity information and heart rate information having been measured in a user-specific performance monitor, and the heart rate information being responsive to the activity level. In one embodiment, the association is formed by taking into account the delay between the activity information and heart rate information.

In 704, the activity information of the user is measured according to an embodiment.

In 706, a performance parameter value is determined using the association between the performance parameter value and activity information in accordance with an embodiment.

In 708, the method ends.

With reference to FIG. 8, the method starts in 800.

In 802, the type of the performance is identified on the basis of activity information.

In 804, a performance type-specific association is formed between the performance type-specific activity information and performance type-specific performance parameter value.

The method ends in 806.

With reference to the embodiment of FIG. 9, the method starts in 900.

In 902, the user's rest state is identified on the basis of ☐ctively information.

In 904, a performance parameter value is determined in the rest state of the user.

The method ends in 906.

The embodiments of the method shown in FIGS. 7, 8, and 9 may be executed by means of a computer process in the processing unit 120 of the performance monitor 100 in accordance with encoded instructions stored in the memory unit 120.

The method steps 702, 802, 804, 902, and 904 may also be executed in the central processing unit 308 of the calculation system 304 as a computer process.

The encoded instructions defining the computer process may be included in a computer software product. The encoded instructions may be transferred by means of a distribution medium that is an electric, magnetic or optic distribution medium, for instance. The distribution medium may be a physical distribution medium, such as memory unit, or optic disc or telecommunications signal.

Even though the invention is above described with reference to the example according to the attached drawings, it is clear that the invention is not limited thereto, but can be modified in many ways within the scope of the attached claims.

What is claimed is:

1. A method of calibrating a user-specific performance monitor, comprising:
   forming an association between an activity level of a user and a performance parameter value proportional to heart rate information of the user by a computing device, wherein the activity level represents the amount of physical activity determined from physical movements generated by the user, the activity level and heart rate information having been measured in a user-specific performance monitor, and the heart rate information being responsive to the activity level; and
   forming an association between the activity level and performance parameter value by associating the activity level with a performance parameter value occurring later than the activity level by an assumed or defined time interval, thereby taking into account the delay between the activity level and heart rate information.

2. A method as claimed in claim 1, wherein the performance parameter characterizes at least one of the following: heart rate frequency, heart rate interval, energy consumption of user, stress level of user.

3. A method as claimed in claim 1, further comprising:
   identifying the type of the performance on the basis of the activity level, the type of performance representing at least one of a sport the user is performing, an activity the user is performing, the rhythmics of the activity the user is performing, and the amplitude of the user's limbs; and
   forming a performance type-specific association between the performance type-specific activity level and performance type-specific performance parameter value.

4. A method as claimed in claim 1, further comprising:
   identifying the user's rest state on the basis of activity level by identifying the user's rest state when the activity level is less than a threshold value during a predefined time interval; and
   determining a performance parameter value in the rest state of the user.

5. A user-specific performance monitor, comprising:
   performance parameter determination means configured to determine a performance parameter value proportional to heart rate information of a user;
   activity measurement means for measuring an activity level of the user, wherein the activity level represents physical activity expressed by physical movements generated by the user; and
   association means for forming an association between the activity level and performance parameter value proportional to the heart rate information that is responsive to the activity level, wherein the association means is configured to form the association between the activity level and performance parameter value by associating the activity level with a performance parameter value occurring later than the activity level by an assumed or defined time interval, thereby taking into account the delay between the activity level and heart rate information.

6. A user-specific performance monitor as claimed in claim 5, wherein the performance parameter characterizes at least one of the following: heart rate frequency, heart rate interval, energy consumption of user, stress level of user.

7. A user-specific performance monitor as claimed in claim 5, further comprising identification means for identifying the type of the performance on the basis of the activity level, the type of performance representing at least one of a sport the user is performing, an activity the user is performing, the rhythmics of the activity the user is performing, and the amplitude of the user's limbs; and
   wherein the association means is configured to form a performance type-specific association between the performance type-specific activity level and performance type-specific performance parameter value.

8. A user-specific performance monitor as claimed in claim 5, further comprising rest state identification means for identifying a rest state of the user on the basis of the activity level by identifying the user's rest state when the activity level is less than a threshold value during a predefined time interval; and
   wherein the performance parameter determination means is configured to determine the performance parameter value in the rest state of the user.

9. A non-transitory computer-readable medium comprising encoded instructions for executing a computer process in a digital processor, the computer process being suitable for calibrating a user-specific performance monitor by:
   forming an association between an activity level of a user and a performance parameter value proportional to the heart rate information of the user, wherein the activity level represents physical activity expressed by physical movements generated by the user, the activity level and heart rate information having been measured in the user-specific performance monitor, and the heart rate information being responsive to the activity level; and
   forming the association between the activity level and the performance parameter value by associating the activity level with a performance parameter value occurring later than the activity level by an assumed or defined time interval, thereby taking into account the delay between the activity level and heart rate information.

10. A non-transitory computer-readable medium as claimed in claim 9, wherein the performance parameter characterizes at least one of the following: heart rate frequency, heart rate interval, energy consumption of user, stress level of user.

11. A non-transitory computer-readable medium as claimed in claim 9, comprising encoded instructions for executing a computer process in a digital processor, the computer process being suitable for calibrating a user-specific performance monitor by:

identifying the type of the performance on the basis of activity level, the type of performance representing at least one of a sport the user is performing, an activity the user is performing, the rhythmics of the activity the user is performing, and the amplitude of the user's limbs; and forming a performance type-specific association between the performance type-specific activity level and performance type-specific performance parameter value.

12. A non-transitory computer-readable medium as claimed in claim 9, further comprising encoded instructions for executing a computer process in a digital processor, the computer process being suitable for calibrating a user-specific performance monitor by:

identifying the user's rest state on the basis of activity level by identifying the user's rest state when the activity level is less than a threshold value during a predefined time interval; and determining the performance parameter value in the rest state of the user.

* * * * *

UNITED STATES PATENT AND TRADEMARK OFFICE
CERTIFICATE OF CORRECTION

PATENT NO. : 7,917,198 B2
APPLICATION NO. : 11/803713
DATED : March 29, 2011
INVENTOR(S) : Ahola et al.

It is certified that error appears in the above-identified patent and that said Letters Patent is hereby corrected as shown below:

IN THE PATENT:

Column 3, line 4:

Now reads: "encoded ▫ctive▫tions stored in the"

Should read: -- encoded instructions stored in the --

Column 6, line 18:

Now reads: "value did not exits"

Should read: -- value did not exist --

Column 8, line 67:

Now reads: "▫ctively information."

Should read: -- activity information. --

Signed and Sealed this
Twenty-eighth Day of August, 2012

David J. Kappos
*Director of the United States Patent and Trademark Office*